United States Patent [19]

Korthoff

[11] Patent Number: 5,089,010

[45] Date of Patent: *Feb. 18, 1992

[54] SURGICAL NEEDLE-SUTURE ATTACHMENT POSSESSING WEAKENED SUTURE SEGMENT FOR CONTROLLED SUTURE RELEASE

[75] Inventor: Herbert W. Korthoff, Westport, Conn.

[73] Assignee: United States Surgical Corporation, Norwalk, Conn.

[*] Notice: The portion of the term of this patent subsequent to Jan. 28, 2009 has been disclaimed.

[21] Appl. No.: 532,953

[22] Filed: Jun. 4, 1990

Related U.S. Application Data

[63] Continuation-in-part of Ser. No. 413,240, Sep. 27, 1989.

[51] Int. Cl.⁵ .................................... A61B 17/00
[52] U.S. Cl. ..................... 606/224; 606/227
[58] Field of Search ................ 606/224–228

[56] References Cited

U.S. PATENT DOCUMENTS

| | | |
|---|---|---|
| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar ........................ 606/226 |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ..................... 606/226 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,704 | 7/1968 | Dery . |
| 3,416,534 | 12/1968 | Quinn . |
| 3,799,169 | 3/1974 | Beroff et al. . |
| 3,835,912 | 9/1974 | Kristensen et al. . |
| 3,875,946 | 4/1975 | Duncan . |
| 3,880,167 | 4/1975 | Hardwick . |
| 3,890,975 | 6/1975 | McGregor . |
| 3,910,282 | 10/1975 | Messer et al. . |
| 3,918,455 | 11/1975 | Coplan ........................ 606/225 |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter ........................ 606/227 |
| 3,980,177 | 9/1976 | McGregor ........................ 606/227 |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss . |
| 4,127,133 | 11/1978 | Martinez . |
| 4,169,477 | 10/1979 | Bokros . |
| 4,359,053 | 11/1982 | Benjamin . |
| 4,411,654 | 10/1983 | Boarini et al. ..................... 604/165 |
| 4,596,728 | 6/1986 | Yang et al. . |
| 4,624,879 | 11/1986 | Van Dijck et al. . |
| 4,672,734 | 6/1987 | Kawada et al. . |
| 4,792,336 | 12/1988 | Hlavaceh et al. ..................... 623/13 |
| 4,805,292 | 2/1989 | Noguchi ........................ 29/445 |

FOREIGN PATENT DOCUMENTS 0358451  3/1990  European Pat. Off. .
2432861  3/1980  France .

OTHER PUBLICATIONS

Raychem Corporation Product specification RT-850 for Thermofit ™ Kynar Tubing dated Mar. 6, 1984.

Primary Examiner—Stephen C. Pellegrino
Assistant Examiner—Gary Jackson
Attorney, Agent, or Firm—Thomas R. Bremer; Peter G. Dilworth; Rocco S. Barrese

[57] ABSTRACT

A combined surgical needle-suture device and a method for manufacturing the device employ a shrinkable tubing to connect the needle to a suture possessing a weakened segment. Separation of the needle from the suture is achieved by providing a weakened suture segment and applying a rupturing force to the suture within a predetermined range.

28 Claims, 4 Drawing Sheets

SURGICAL NEEDLE-SUTURE ATTACHMENT POSSESSING WEAKENED SUTURE SEGMENT FOR CONTROLLED SUTURE RELEASE

CROSS REFERENCE TO RELATED APPLICATION

This application is a continuation-in-part of commonly assigned, copending U.S. patent application Ser. No. 413,240, filed Sept. 27, 1989.

BACKGROUND OF THE INVENTION

The present invention relates to a method for attaching a surgical needle to a suture to provide a combined surgical needle-suture device possessing controlled suture release characteristics and, more particularly, to such a method in which a shrinkable tubing is employed to secure the needle to the suture.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopoeia* (USP). The *United States Pharmacopoeia* prescribes minimum individual pull-out forces and minimum average pull-out forces as measured for five needle-suture combinations. The minimum pull-out forces for both standard and removable needle-suture attachment set forth in the *United States Pharmacopoeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle silconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

Commonly assigned, copending U.S. patent application Ser. No. 413,240, filed Sept. 27, 1989, of which the present application is a continuation-in-part, describes and claims a combined surgical needle-suture device and surgical needle-suture attachment method which overcomes the aforementioned drawbacks of the previously known needle-suture combinations and needle-suture attachment methods. In accordance with said application, a combined surgical needle-suture device is provided in which a surgical needle having a shank of reduced cross-section is attached to a suture through a shrinkable tubing, or micro-ferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

Minimum average pull-out forces for various sizes of combined surgical needle-suture devices are set forth in the *United States Pharmacopoeia* and are as follows:

| Suture Size | Average Pull-Out Force/Ounces |
| --- | --- |
| 8/0 | 2.39 |
| 7/0 | 3.20 |
| 6/0 | 5.92 |
| 5/0 | 7.97 |
| 4/0 | 15.97 |
| 3/0 | 23.63 |
| 2/0 | 38.80 |
| 1/0 | 52.89 |
| 1 | 63.48 |
| 2 and larger | 63.48 |

U.S. Pat. No. 3,875,946, referred to supra, describes needle-suture combinations said to exhibit suture pull-out values that are substantially less than those given by the *United States Pharmacopoeia* as set forth above. According to U.S. Pat. No. 3,875,946, employing the procedure described therein, combined surgical needle-suture devices can be obtained with the following average pull out forces:

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26. |

These pull-out forces are obtained by prestressing the suture, i.e., by applying tension to the suture after the tip of the suture has been inserted into an axial bore, or recess, formed in the blunt end of the needle and the needled suture has been swaged so that the force required to pull the suture out of the recess exceeds the minimum limits on needle attachment set forth in the *United States Pharmacopoeia* but is less than the actual tensile strength of the suture used. As the suture is pulled from the needle during application of the tensioning force, the force required to move the suture relative to the swaged section decreases. When the tensioning force required to move the end of the suture relative to the needle recess drops to the desired pull-out value, the tension is released.

The foregoing procedure is said to permit better control of the resulting needle-suture device in that the force required to separate a suture of a particular size from its attached needle is uniform.

Other approaches to achieving controlled needle-suture separation are described in aforementioned U.S. Pat. Nos. 3,943,933 and 3,949,756, the contents of which are incorporated by reference herein. According to U.S. Pat. No. 3,943,933, a needle-suture combination provided with a radiation-weakened suture segment adjacent the point of attachment of the suture to the needle permits a surgeon to separate the needle from the suture by a sharp tug. In U.S. Pat. No. 3,949,756, a suture provided with a weakened segment in the form of a notch adjacent the point of attachment of the suture to the needle likewise permits separation of the needle from the suture by a sharp tug.

SUMMARY OF THE INVENTION

In accordance with the present invention, there is provided a method for attaching a surgical needle to a suture to provide a combined surgical needle-suture device which comprises:
  a) providing a surgical needle possessing a shank end of reduced cross-section and a suture possessing a weakened segment adjacent its tip region;
  b) placing a shrinkable tubing around the reduced diameter shank end of the needle and the tip of the suture such that the weakened segment of the suture is positioned beyond, but proximate to, the tubing; and,
  c) applying energy to the shrinkable tubing to bring the tubing into engagement with the needle shank and the tip of suture thereby providing the combined surgical needle-suture device.

In addition to the foregoing surgical needle-suture attachment method, the present invention includes the resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a combined surgical needle-suture method and resulting surgical needle-suture device featuring controlled suture release. The invention has application to any suture material whether absorbable or non-absorbable, natural or synthetic, braided or monofilament, and to any needle material and configuration whether straight or curved.

Figure 1:
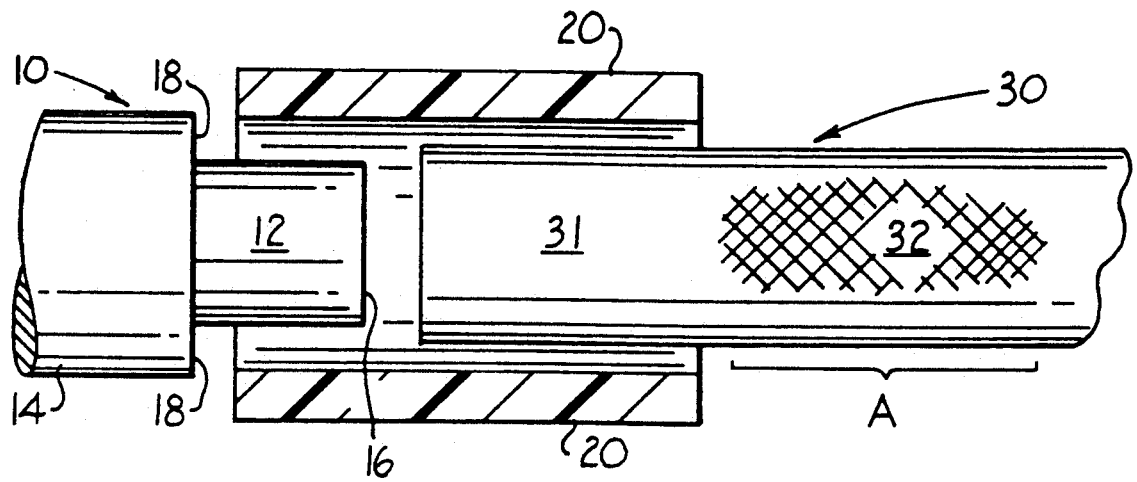
FIG. 1 is a side cross-sectional view of a surgical needle possessing a reduced shank and a suture possessing a radiation-weakened segment adjacent its tip region with a shrinkable tubing positioned around the reduced shank of the needle and the tip of the suture (prior to engagement of the tubing with the needle and suture)
Figure 2:
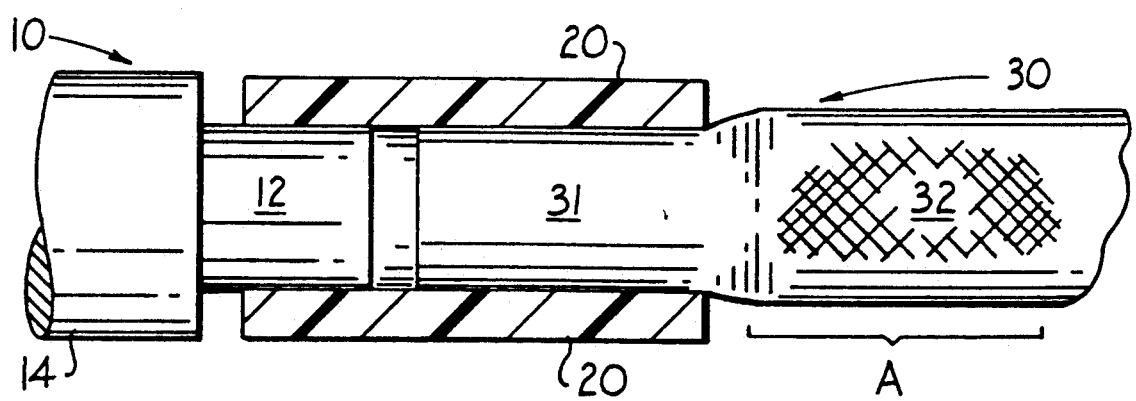
FIG. 2 is a side cross-sectional view of the needle-suture combination of FIG. 1 following shrinking of the tubing to effect engagement of the needle shank and the suture tip.
Figure 3:
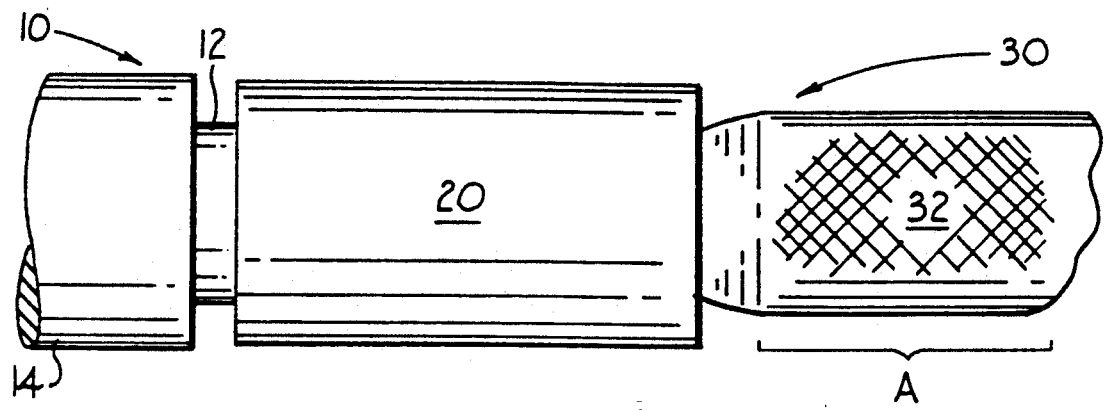
FIG. 3 is a side view of the combined surgical needle-suture device of FIG. 2.
Figure 5:
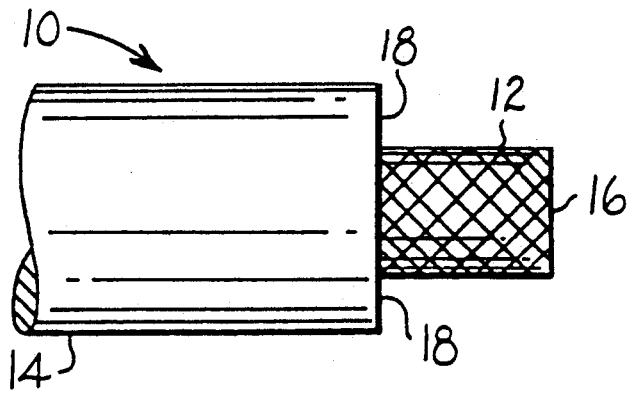
FIG. 5 is a side of an alternative embodiment of the present invention in which the needle shank is scored.
Figure 6:
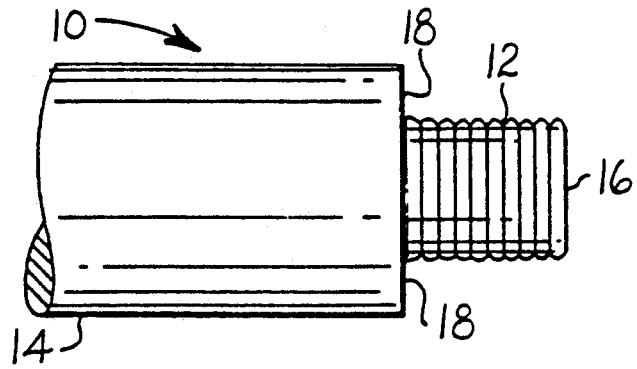
FIG. 6 is a side view of an alternative embodiment of an alternative embodiment of the present invention in which the needle shank is ribbed.
Figure 7:
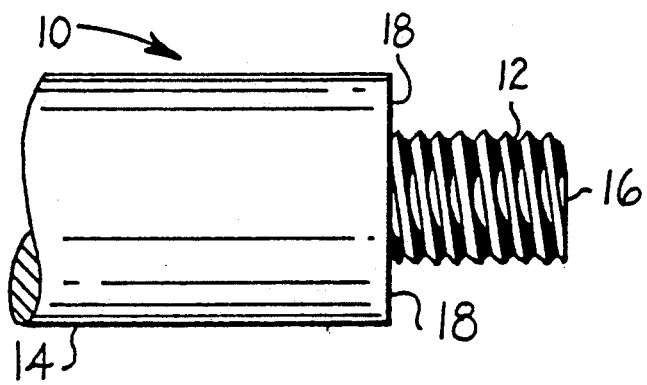
FIG. 7 is a side view of an alternative embodiment of the present invention in which the needle shank is threaded.
Figure 8:
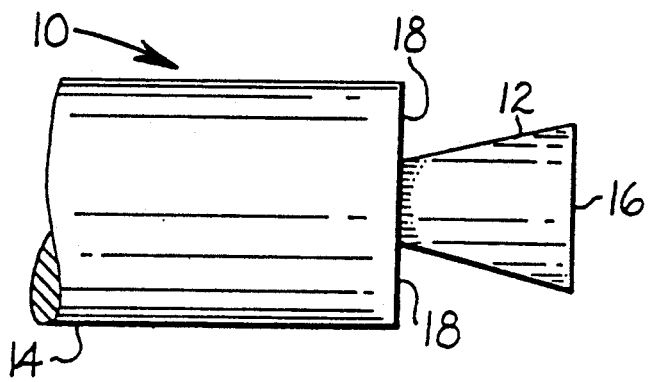
FIG. 8 is a side view of an alternative embodiment of the present invention in which the needle shank is tapered to expand in a direction away from a remainder of said needle.
Figure 9:
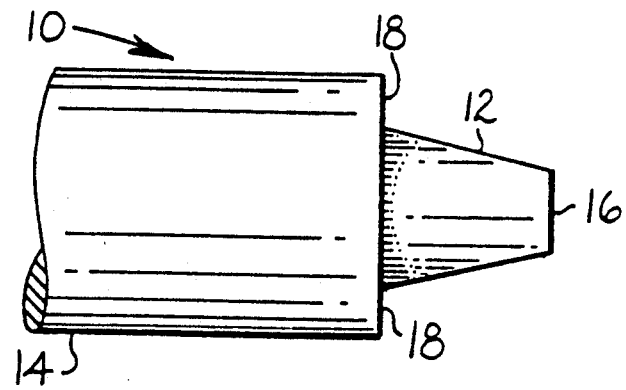
FIG. 9 is a side view of an alternative embodiment of the present invention in which the needle shank is tapered to expand in a direction towards the remainder of the needle.

Referring to FIGS. 1-3, needle 10 has a reduced cross-sectional diameter at its shank end 12 relative to the remainder of needle 14. The diameter of shank end 12 can be reduced by any conventional means, e.g., by machining on a lathe. Typically, shank end 12 has a diameter from 10 to 65% smaller than the remaining portion 14 of the needle, and preferably from 25 to 50% smaller. It is also possible to provide shank end 12 with a texturized surface to facilitate gripping by shrinkable tubing 20. For example, shank end 12 can be scored, ribbed or threaded, in whole or in part (FIGS. 5-7 respectively). It may also be desirable to taper shank end 12 such that its butt, or distal, end 16 is of greater cross-sectional diameter than the cross-sectional diameter of shank end 12 in the region of shoulder 18, or vice versa (FIGS. 8 and 9 respectively). Shank end 12 is placed within tubing 20 as shown in FIG. 1.

Suture 30 possesses a tip region 31 for subsequent engagement by tubing 20 and adjacent to the tip region, a radiation-weakened segment 32 throughout region A of the suture. As disclosed in aforementioned U.S. Pat. No. 3,943,933, the load at which suture 30 will rupture at its radiation-weakened segment 31, i.e., within region A, can be made to vary from 3 to 26 ounces depending upon the size of the suture.

The radiation-weakening of suture segment 32 can be achieved by exposure of region A of the suture which is adjacent its tip region 31 and is at or just beyond the end of shrinkable tubing 20 to a sufficient dose of beta or gamma radiation to reduce the tensile strength in the irradiated segment to a desired value. This irradiation procedure will ordinarily be accomplished prior to providing the needle-suture configuration shown in FIG. 1. The necessary dose, or exposure, to achieve the desired weakening of suture segment 32 is dependent on the nature of the suture material and its diameter and upon the degree of weakening desired. In the case of sutures of small diameter which have rupture values within the desired range, radiation-weakening is, of course, unnecessary.

For suture materials readily susceptible to radiation-weakening in sutures of small diameters and requiring only slight weakening to be within the desired range of rupture values, useful radiation-weakening may be achieved with radiation doses as low as about 5 megarads. For suture materials which are more difficult to weaken by irradiation in sutures of larger diameter, it may be necessary to provide a dose of 200 megarads, or more, before the rupture strength of the suture is reduced to a practical value for easy separation of the needle from the suture.

Thus, with increased radiation dosage, radiation-weakened segment 31 can be made to undergo rupture within the following average range of force for the suture size indicated:

| Suture Size | Average Rupture Force | |
| --- | --- | --- |
| | Ounces | Pounds |
| 8/0 | 1-2 | .0625-.125 |
| 7/0 | 1-3 | .0625-.1875 |
| 6/0 | 2-5 | .125-.3125 |
| 5/0 | 3-7 | .1875-.4375 |
| 4/0 | 3-15 | .1875-.9375 |
| 3/0 | 3-23 | .1875-1.4375 |
| 2/0 | 3-26 | .625-1.625 |
| 1/0 | 10-26 | .625-1.625 |
| 1 | 10-26 | .625-1.625 |
| 2 and larger | 10-26 | .625-1.625 |

The radiation used for localized suture weakening in accordance with this invention can comprise either a high energy electron beam, e.g., of the type produced by a linear electron accelerator, or a high energy beam of electromagnetic radiation of extremely short wave length, e.g., of the type generated by cobalt-60 or by a high energy X-ray generator. These forms of radiation are conventionally referred to as "beta" and "gamma" radiation, respectively. An electron accelerator capable of delivering a large dose of energy in a short time is preferred.

Radiation generators suitable for use in this invention include those which have been used by manufacturers of needle-suture combinations for sterilization purposes. For localized suture weakening, however, the arrangement is altered so that the suture passes transversely across the path of the beam instead of longitudinally, thereby isolating the radiation effect to a small segment of the suture length, and the arrangement is also modified to permit a plurality of passes of the suture segment to be weakened under the radiation beam and to thereby subject the segment to the cumulative dosage of such a plurality of passes. The sutures may be aligned parallel to each other in a grooved holder encased within a lead casing or other suitable shielding except for an exposed open slot which permits the radiation to pass through the casing and act upon a short segment of each suture at or near its junction to its needle.

Fiber-forming materials suitable for sutures which are useful in the practice of this embodiment of the invention include cellulose and cellulose esters including cotton, linen, viscose rayon and cellulose acetate; polyolefins including polypropylene and polyethylene; vinyl polymers including polyvinyl alcohol, polyvinyl acetate and polyvinylidene chloride; acrylic polymers such as polyacrylonitrile and homopolymers and copolymers of lactide and glycolide.

Figure 4:
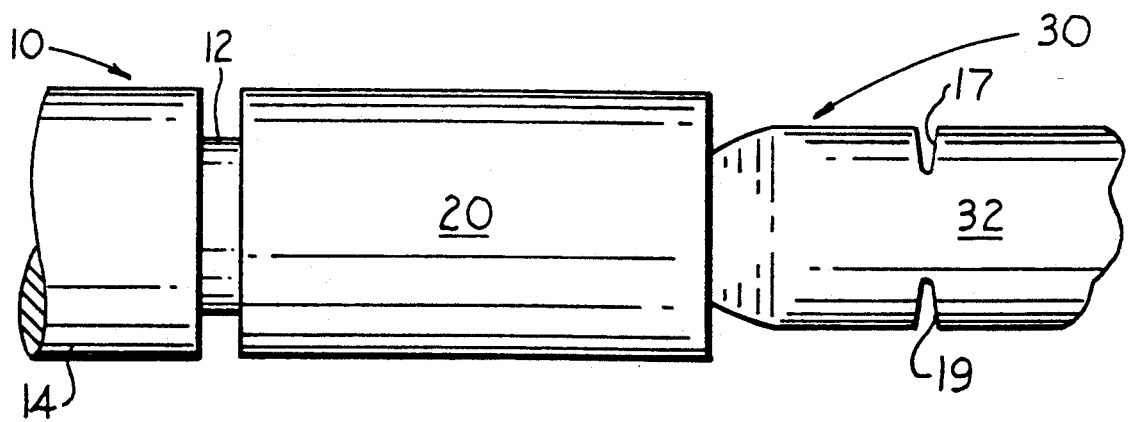
FIG. 4 is a side view of another embodiment of the combined surgical needle-suture device of this invention in which the weakened suture segment is provided as a pair of opposed notches.

As an alternative to a radiation-weakened suture segment and as shown in FIG. 4, suture 30 can be provided with a mechanically weakened segment 32, e.g., provided as a pair of opposed notches 17 and 19 as described in U.S. Pat. No. 3,949,756. Notching or similar mechanical discontinuities can be formed in suture segment 32 by application of at least one cutting edge thereto or by application of at least one abrasive surface to the suture surface at the desired location with relative movement between the abrasive and suture surfaces.

According to U.S. Pat. No. 3,949,756, a preferred notching device has two parallel blades facing each other and firmly set with a measured gap between them. As the suture is moved transversely to the blade direction, two straight notches are formed facing each other with a preset width of unnotched suture between them.

In another embodiment, also described in U.S. Pat. No. 3,949,756, the needle-suture combination is held within a groove and against the bed thereof. A knife-edge is moved transversely into the area of the groove with a stroke that is restricted by a stop so that a desired distance is maintained between the bed of the groove and the end of the knife stroke whereby a single notch is formed on one side of the suture and a controlled portion of the suture on the opposite side remains uncut, or unnotched.

In yet other embodiments, notching is achieved in a similar manner except that a pair of rotating abrasive wheels or a single rotating abrasive wheel is used in place of the knife edges, or knife edge(s).

Other embodiments provide for notching about the periphery of suture 30 by rotating the suture in contact with a knife edge or with a grinding wheel until a circumferential notch of the desired depth is formed.

The sutures suitable for use in the preparation of the notched needle-suture combination of FIG. 4 include both monofilaments and multifilament structures such as braided, twisted and covered sutures. Suitable suture materials include collagen (including catgut and extruded collagen), silk, cotton, linen and synthetic polymers including nylon, polypropylene and polyesters such as polyethylene terephthalate and homopolymers and copolymers of lactide and glycolide.

When suture 30 is notched, the remaining strength of the suture is less than would be expected if the strength and cross-sectional areas were directly proportional. Usually, the rupture strength of the suture at the notched segment is only about $\frac{1}{2}$.5 to about $\frac{1}{2}$.0 times the rupture strength that would be expected based on the relative areas of the original suture cross section and the cross section of the notched portion of the suture at the location of the notch or notches.

With multifilament sutures, the entire cross-sectional area of the suture is not made up of suture material since there is, of necessity, some free space between the suture strands. The proportion of the total cross-sectional area of a suture which is occupied by the suture strands is called "suture density" and generally runs in braided sutures, for example, from about 0.70 to about 0.95, and most usually from about 0.80 to about 0.92.

The suture densities of braided structures and suture densities in general are calculated from the volume of the sample of the suture and the volume of the fiber herein in accordance with the formula:

$$D = \frac{F}{S}$$

in which S is the volume of the suture, F is the volume of the fiber, and D is the suture density.

For convenience, it is best to determine volumes in samples at fixed lengths of 9,000 meters, r $9 \times 10^5$ centimeters. This is convenient because fiber denier is defined as weight in grams per 9,000 meters. At this length, the volume of the suture in cubic centimeters is:

$$\frac{\pi d^2 (9 \times 10^5)}{4}$$

where d is the diameter of the suture in centimeters. The volume in cubic centimeters of the individual fibers, F. at the same length would be:

$$\frac{\text{number of strands} \times \text{denier per strand}}{r}$$

or $$\frac{\text{denier of suture}}{r}$$

where r is the density of the suture material in grams per cubic centimeter. The load at which a notched suture will rupture may be estimated from the equation:

$$P = \frac{ATD}{K}$$

wherein
P is the rupture load, in pounds;
T is the tensile strength of the suture material, in pounds per square inch;
A is the area, in square inches, remaining unnotched at the notched portion of the suture;
D is the suture density of the suture, being unity in the case of a monofilament; and,
K is a constant factor, initially determined empirically for each suture material and represents the degree of weakening at the notched portion of the suture over and above the weakening to be expected from its reduced area. As a useful approximation, K may be taken at values in the range of 2.0 to 2.5 for natural and synthetic polymeric suture materials.

As in the case of the irradiated suture segment embodiment of FIGS. 1-3, it is usually desired that the notch-weakened suture of FIG. 4 be rupturable at its notched portion by a force of from about 1 ounce to about 26 ounces, or from about 0.0625 to about 1.625 pounds, and these limits may be inserted in the above equation as the limiting values for rupture load P. Selecting an average value for P of 0.8 pounds provides leeway for differences in individual sutures and for difference in their notching and assures rupture strengths within the desired range for most of the notched sutures.

In general, the specific rupture values for the notch-weakened suture can be the same as those for the irradiated suture as set forth above.

Returning to FIG. 1, suture 30 is positioned within shrinkable tubing 20 with suture tip 31 abutting or separated a short distance from distal end 16 of shank 12 and weakened suture segment 32 positioned at, or a short distance beyond, the end of tubing 20. As shown in FIG. 1, suture 30 may initially be of uniform cross-section throughout its length. Alternatively, tip region 31 of suture 30, i.e., the region inserted into tubing 20, may be of reduced cross-section relative to the remainder of suture 30, e.g., by tipping the suture tip with an adhesive or resinous tipping agent while suture 30 is under tension. (See, e.g., Canadian Patent No. 1,009,532.) Resin tipping may be desirable to prevent brooming of the suture, particularly in the case of multifilament braided sutures, and/or to rigidify the end of the suture to facilitate its handling during attachment. Reducing the diameter of suture tip 31, as by tipping under tension, may be desirable to allow a suture of larger diameter, i.e. a suture diameter equal to the diameter of the needle to which it is attached, to be more efficiently attached to the needle using the shrinkable tubing of the present invention. It is not necessary according to the present invention, however, to reduce the diameter of suture tip region 31 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of suture tip region 31, thereby minimizing the importance of suture tipping.

After shrinkable tubing 20 is placed around shank end 12 of needle 10 and tip region 31 of suture 30, energy is applied to tubing 20. In response to this energy, tubing 20 contracts or shrinks and engages shank end 12 and suture tip 31. The overall length of tubing 20 may also be affected by the application of energy, e.g., the length of tubing 20 may reduce. Thus, the shrinking of tubing 20 brings the inner surface of tubing 20 into engagement with shank end 12 and suture tip 31, thereby securing suture 30 to needle 10. Suitable energy sources include heat (convective or conductive), radiation, microwave energy, etc.

As shown in FIGS. 1-2, shrinkable tubing 20 is simultaneously placed around both suture tip 31 and shank end 12 of needle 10 in one embodiment of the present invention. It is preferable, however, to sequentially secure tubing 20 to needle 10 and suture tip 31. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, tip 31 of suture 30 is inserted into tubing 20 and additional energy is applied thereto. Sequential shrinkage of tubing 20 makes it possible to vary the amount of energy used in securing tubing 20 to shank end 12 and suture tip 31, respectively, and to limit the exposure of suture 30 to energy during the attachment process. It may also be desirable to cool suture 30 in the region outside tubing 20 to prevent any undesirable degradation thereof, e.g., with a cold air curtain.

As shown in FIGS. 2-4, the shrinkage of tubing 20 typically compresses tip region 31 of suture 30 to some extent. This is particularly true where the suture is a braided, multi-filament material having void spaces in its structure. For example, tubing 20 may compress suture tip 31 by as much as 30 to 35% for a braided, synthetic absorbable suture and by a minimal amount for a relatively stiff material such as a monofilament surgical gut.

Shrinkable tubing 20 can be manufactured from any material which shrinks, i.e., reduces in diameter, in response to the application of energy. Suitable materials include "memory metals," e.g., nickel-titanium mixtures, nickel-iron-titanium mixtures, or copper based materials, as are well known in the art (see, e.g., U.S. Pat. Nos. 3,759,552, 3,801,954, 4,198,081, and 4,773,680), and shrinkable plastic materials, such as polyvinylidene fluoride materials available from Raychem Corporation, Menlo Park, California, under the tradename Kynar. In the case of shrinkable plastic materials, the tubing is typically extruded such that the inner diameter is less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink, or "recover", to its original extruded inner diameter in response to the application of a predetermined amount of energy.

The amount of energy applied to the tubing to effect the desired attachment, i.e., diameter reduction, depends upon the chemical characteristics of the tubing material and the relative dimensions of the tubing and the shank end of the needle and the suture. For example, one polyvinylidene fluoride material available from Raychem Corporation (RT-850) shrinks at temperatures greater than 175° C., and is adapted to recover to about 50% of its radially expanded inner diameter. In such case, tubing 20 can be brought into engagement with shank end 12 of needle 10 and suture tip 31, either simultaneously or sequentially, by heating tubing 20 to a temperature above 175° C. Tubing 20 can be heated through contact with a hot gas stream or with heated dies, or by other heating means. Typically, the outer diameters of shank end 12 and suture tip 31 are greater than the fully recovered diameter of tubing 20, e.g., greater than 50% of the initial inner diameter of tubing 20 for the RT-850 material, such that tubing 20 engages shank end 12 and suture tip 31. It is preferred that the attachment conditions be controlled such that the tubing remains secured to the needle once the suture is detached.

The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method is also much more efficient from a processing and inventory control standpoint. For example, the tubing can be removed from a needle and the needle attached to a fresh suture, e.g., in instances where the suture and/or attachment properties of the initial suture-needle combination are outside specifications. In many instances, the suture can also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations. Moreover, the needle-suture combinations are atraumatic and advantageously exhibit flexibility in the attachment region.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture to provide a combined surgical needle-suture device which comprises:
   a) providing a surgical needle possessing a shank end of reduced cross-section and a suture possessing a weakened segment adjacent its tip region;
   b) placing a shrinkable tubing around the reduced diameter shank end of the needle and the tip of the suture such that the weakened segment of the suture is positioned beyond, but proximate to, the tubing; and,
   c) applying energy to the shrinkable tubing to bring the tubing into engagement with the needle shank and the tip of suture thereby providing the combined surgical needle-suture device.

2. The method of claim 1 wherein the weakened segment of the suture is obtained by irradiating the suture in the region of the segment with a suture-weakening dosage of radiation.

3. The method of claim 2 wherein the average force required to rupture the irradiation-weakened suture segment is within the following range for the suture indicated

| Suture Size | Average Rupture Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26. |

4. The method of claim 2 wherein the suture is fabricated from a fiber-forming material selected from the group consisting of cellulose, cellulose ester, polyolefin, vinyl polymer, acrylic polymer, lactide homopolymer, lactide copolymer, glycolide polymer and glycolide copolymer.

5. The method of claim 1 wherein the suture is a monofilament suture.

6. The method of claim 1 wherein the suture is a braided suture.

7. The method of claim 1 wherein the weakened segment of the suture is obtained by forming a suture-weakening notch in the segment.

8. The method of claim 7 wherein the average rupture force required to rupture the notch-weakened suture segment is within the following range for the suture indicated

| Suture Size | Average Rupture Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26. |

9. The method of claim 7 wherein the suture is fabricated from a fiber-forming material selected from the group consisting of collagen, silk, cotton, linen, nylon, polypropylene, polyethylene terephthalate, lactide homopolymer, lactide copolymer, glycolide homopolymer and glycolide copolymer.

10. The method of claim 1 wherein the shrinkable tubing is a memory metal or shrinkable plastic.

11. The method of claim 1 wherein the shrinkable tubing is a shrinkable polyvinylidene fluoride material.

12. The method of claim 1 wherein the step of applying energy further comprises applying energy to shrink the shrinkable tubing into engagement with the needle shank and thereafter applying energy to shrink the shrinkable tubing into engagement with the tip of the suture.

13. A combined surgical needle-suture device which comprises:
   a) a surgical needle possessing a shank end of reduced cross-section;
   b) a suture possessing a weakened segment adjacent its tip region;
   c) a shrinkable tubing around the reduced diameter shank end of the needle and the tip of the suture such that the weakened segment of the suture is positioned beyond, but proximate to the tubing;
   the tubing being shrunk around the reduced diameter shank end of the needle and the tip region of the suture thereby providing the combined surgical needle-suture device.

14. The combined surgical needle-suture device of claim 13 wherein the weakened segment of the suture is obtained by irradiating the suture in the region of the segment with a suture-weakening dosage of radiation.

15. The combined surgical needle-suture device of claim 14 wherein the average force required to rupture the irradiation-weakened suture segment is within the following range for the suture indicated

| Suture Size | Average Rupture Force/Ounces |
|---|---|
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26. |

16. The combined surgical needle-suture device of claim 14 wherein the suture is fabricated from a fiber-forming material selected from the group consisting of cellulose, cellulose ester, polyolefin, vinyl polymer, acrylic polymer, lactide homopolymer, lactide copolymer, glycolide polymer and glycolide copolymer.

17. The combined surgical needle-suture device of claim 13 wherein the suture is a monofilament suture.

18. The combined surgical needle-suture device of claim 13 wherein the suture is a braided suture.

19. The combined surgical needle-suture device of claim 13 wherein the weakened segment of the suture is obtained by forming a suture-weakening notch in the segment.

20. The combined surgical needle-suture device of claim 19 wherein the average rupture force required to rupture the notch-weakened suture segment is within the following range for the suture indicated

| Suture Size | Average Rupture Force/Ounces |
|---|---|
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26. |

21. The combined surgical needle-suture device of claim 19 wherein the suture is fabricated from a fiber-forming material selected from the group consisting of collagen, silk, cotton, linen, nylon, polypropylene, polyethylene terephthalate, lactide homopolymer, lactide copolymer, glycolide homopolymer and glycolide copolymer.

22. The combined surgical needle-suture device of claim 13 wherein the shrinkable tubing is a memory metal or shrinkable plastic.

23. The combined surgical needle-suture device of claim 13 wherein the shrinkable tubing is a shrinkable polyvinylidene fluoride material.

24. The combined surgical needle-suture device of claim 13, wherein the shank end of the needle is provided with a texturized surface to facilitate gripping by said shrinkable tubing.

25. The combined surgical needle-suture device of claim 24, wherein the shank end of the needle is scored, ribbed or threaded, in whole or in part.

26. The combined surgical needle-suture device of claim 13, wherein said shank end of reduced cross-section forms a shoulder with a remainder of said needle.

27. The combined surgical needle-suture device of claim 26, wherein said shank end is tapered to expand in a direction away from said shoulder, such that a distal end thereof is of greater cross-sectional diameter than cross-sectional diameter in a region of said shoulder.

28. The combined surgical needle-suture device of claim 26, wherein said shank end is tapered to expand in a direction towards said shoulder, and that a distal end thereof is of smaller cross-sectional diameter than cross-sectional diameter in a region of said shoulder.

* * * * *